United States Patent [19]

Magnusson

[11] Patent Number: 5,620,475
[45] Date of Patent: Apr. 15, 1997

[54] EXTRACORPOREALLY CONTROLLABLE MEDICAL IMPLANT AND METHOD FOR OPERATING SAME

[75] Inventor: Peter Magnusson, Nacka, Sweden

[73] Assignee: Siemens Elema AB, Solna, Sweden

[21] Appl. No.: 421,780

[22] Filed: Apr. 14, 1995

[30] Foreign Application Priority Data

Apr. 25, 1994 [SE] Sweden ................... 9401402

[51] Int. Cl.$^6$ ................... A61N 1/08
[52] U.S. Cl. ................... 607/30
[58] Field of Search ................... 607/30, 9

[56] References Cited

U.S. PATENT DOCUMENTS 4,428,378  1/1984  Anderson et al. .
4,545,380  10/1985  Schroeppel .
4,651,740  3/1987  Schroeppel .
5,113,859  5/1992  Funke .

Primary Examiner—William E. Kamm
Assistant Examiner—Scott M. Getzow
Attorney, Agent, or Firm—Hill, Steadman & Simpson

[57] ABSTRACT

A medical implant contains a sensor for sensing extracorporeally, manually generated shockwaves and for generating electrical signals, a detector connected to the sensor that, dependent on the electrical signals, emits pulses to a control unit connected to the detector for controlling a function implementing stage. The control unit emits a function signal to the function stage for the implementation of a function of the implant corresponding to a sequence of one or more parameters with reference to two or more pulses in a shockwave sequence, said sequence being identified in the control unit. In a method for controlling a medical implant, shockwaves are manually generated in a sequence and pulses are respectively generated dependent on the shockwaves, a function signal is supplied to a function stage given every identified sequence of one or more parameters referred to two or more pulses and the implant function defined by the identified sequence is then implemented by the function stage.

8 Claims, 1 Drawing Sheet 5,620,475

EXTRACORPOREALLY CONTROLLABLE MEDICAL IMPLANT AND METHOD FOR OPERATING SAME

BACKGROUND OF THE INVENTION

1. Field of the Invention

The present invention is directed to a medical implant and to a method for the control of the medical implant, such as an insulin pump, a heart pacemaker or a defibrillator.

2. Description of the Prior Art

It is known to wirelessly communicate with a medical implant by means of an external programming unit. This ensues, for example, using radio signals. Various settings for the implant can be modified and influenced with the programming unit. Given an insulin pump, it is desirable to be able to modify the dose that is to be administered and the point in time for the administration of the dose and to interrupt a dose that has been started. Given a heart pacemaker, one may modify the stimulation frequency, the thresholds of sampled values and may change the stimulation mode of the heart pacemaker, etc. Given a defibrillator, one may, for example, activate various operating modes. Another important task of the programming unit is to provide the possibility of taking information from the implant. This can be an overview of the signals sensed by the implant.

U.S. Pat. No. 5,113,859 discloses a device for bi-directional (duplex) communication between two modules that, according to one embodiment, are arranged respectively in an implant or in an external programming unit. The communication ensues acoustically with ultrasound signals that are generated by piezocrystals. During the transmission, the crystal is activated by a carrier wave modulated by information. Transmission and reception units are provided both in the implant and in the programming unit. The transmission unit includes an oscillator that generates a sine signal that is used a carrier wave having a carrier wave frequency that lies within the range of 10 Khz through 100 Khz. The oscillator is coded by a pulse signal such that the resultant signal that is communicated to the piezocrystal is composed of bursts of oscillations, with the number of oscillations in every burst being varied according to the coding employed. Provided in every reception unit are a filter, a demodulator and a pulse-shaping unit that restores the pulses, and thus the information that has been transmitted. The apparatus disclosed in U.S. Pat. No. 5,113,859 can be employed to modify various parameters in a heart pacemaker or in a defibrillator or in an implant that is provided for administering a medication. In order to influence the implant disclosed in U.S. Pat. No. 5,113,859, consequently, it is necessary that an external programming unit be used.

Implanted insulin pumps, for example, can be programmed in order to administer a specific quantity of insulin, referred to as a basal flow, with increased insulin doses on certain occasions, often in combination with meals. A further possibility is that the patient himself defines the so-called mealtime doses with a programming unit, by means of which the insulin pump is commanded at self-selected points in time to emit an increased dose with a dose volume that can be selected. This yields greater flexibility for the patient but also means the programming unit must always be carried by the patient. A further disadvantage is that there can be instances when the patient considers it unpleasant or laborious to take out the programming unit in order to administer an insulin dose. For example, this can be at the beach, when visiting a restaurant or some other place where there are many people.

SUMMARY OF THE INVENTION

An object of the present invention is to provide an improved medical implant and an improved method for operating same that eliminate the aforementioned disadvantages of the known technology.

This object is inventively achieved in an implant whose operation is controlled extracorporeally by a series of pulsed shockwaves the implant containing a control device for measuring the time between consecutive pulses and for comparing the measured time interval to a first predetermined and to a second predetermined time interval. All time intervals measured in a control sequence of incoming pulses can be referred to the first or to the second time interval. The resulting sequence of time intervals arising from the comparisons is compared to sequences of time intervals that are stored in the control device and that represent different functions of the medical implant. A sequence of measured time intervals is considered identified when it is among the sequences stored in the control device.

The above object is also achieved in a method for controlling a medical implant including the steps of generating a control sequence of pulses, measuring the time between consecutive pulses and comparing the measured time interval to a first predetermined time interval and to a second predetermined time interval. All time intervals measured in a sequence can be referred to the first or to the second time interval. Further steps of the method include comparing the sequence of the time intervals arising from the comparisons to sequences of time intervals stored in the implant that represent various functions for the medical implant. The sequence of measured time intervals is considered identified when it is among the sequences stored in the implant.

As used herein, "shockwaves" means mechanical waves which are propagated through tissue in the body as a result of an impact to the exterior of the body as can be produced by tapping the body with the hand.

A sequence of shockwaves can be used as the extracorporeally generated control pulse sequence and thus contains short or long time intervals between the generated shockwaves. Various sequences of short and long time intervals are the stored sequences which respectively correspond to individual functions of the implant.

The invention, consequently, results in an implant to which instructions corresponding to various functions of the implant can be transmitted without employing an extracorporeal programming unit. A method for the control of the implant without the use of a programming device is also achieved.

The invention is based on the fact that there are a small number of functions for, for example, insulin pumps that must be frequently carried out. For example, a mealtime dose to be administered may be specified. Because it is now possible to communicate the commands that correspond to these functions without employing a programming unit, the manipulation of the insulin pump is simplified.

The transmission ensues by the patient manually generating a sequence of shockwaves that the implant senses. These can be produced, for example, by clapping or by striking the skin with a hand in the proximity of the implant and thereby generating a sequence of shockwaves corresponding to a function of the implant. This sequence of shockwaves is sensed by the implant, whereby a comparison of the sensed sequence and the sequences stored in the implant that correspond to various functions of the implant is undertaken. When a sensed sequence has been identified, the corresponding function of the implant is implemented.

Since it should be possible to memorize the sequences that are employed, they should not be too numerous or too complicated.

Accordingly, the present invention serves as a complement to a programming unit. Such a unit is still required to initiate more complicated functions of the implant and for taking information out of the implant.

According to a further embodiment of the implant of the invention, the control device measures the time between consecutive pulses and compares the measured time interval to a predetermined threshold. When all time intervals measured for a sequence of pulses fall below this threshold, the control device determines the number of pulses that belong to the sequence and compares this number to numbers stored in the control device that represent various functions of the medical implant. The sequence is considered identified when the number of pulses belonging to the sequence corresponds to one of the numbers stored in the control device. In this embodiment, it is the number of shockwaves in a sequence of shockwaves that identifies the function.

According to another embodiment of the implant of the invention, a signal generator is connected to the control device and to the sensor, and a control signal that is generated by the control device is supplied to the signal generator which in turn, generates a signal dependent on the control signal, this latter signal activating the sensor to emit an extracorporeally detectable signal. As a result, it is possible for the patient to verify that generated shockwaves have led to the identification of the desired sequence, resulting in enhanced safety for the patient.

In an advantageous embodiment of the method of the invention, a first sequence of shockwaves is generated in order to prepare the implant to accept a sequence of shockwaves corresponding to a function of the implant. A second sequence of shockwaves that defines a function of the implant is generated in the implant. A control signal corresponding to the second sequence of shockwaves is generated in the implant and supplied to a sensor in the implant in order to activate the sensor to emit extracorporeally detectable signals corresponding to the second sequence for confirmation that the generated second sequence corresponds to the intended sequence. When this is the case, a third sequence of shockwaves is generated as a command that the function corresponding to the second sequence should be implemented. The control device emits a function signal to a function unit for the implementation of the function corresponding to the second sequence when the accepted third sequence is identified by the control device as a command sequence.

The implant, accordingly, is only enabled with the first sequence for accepting the second sequence that defines the function that the patient wants to carry out. The patient orders the implementation of the function with the third sequence after reception of the acknowledge that the desired measure sequence has been identified in the implant. This eliminates the risk that an erroneous measure will be implemented.

DESCRIPTION OF THE DRAWINGS

The single FIGURE is a block diagram of an exemplary embodiment of a medical implant constructed and operating in accordance with the principles of the present invention.

DESCRIPTION OF THE PREFERRED EMBODIMENTS

Figure 1:
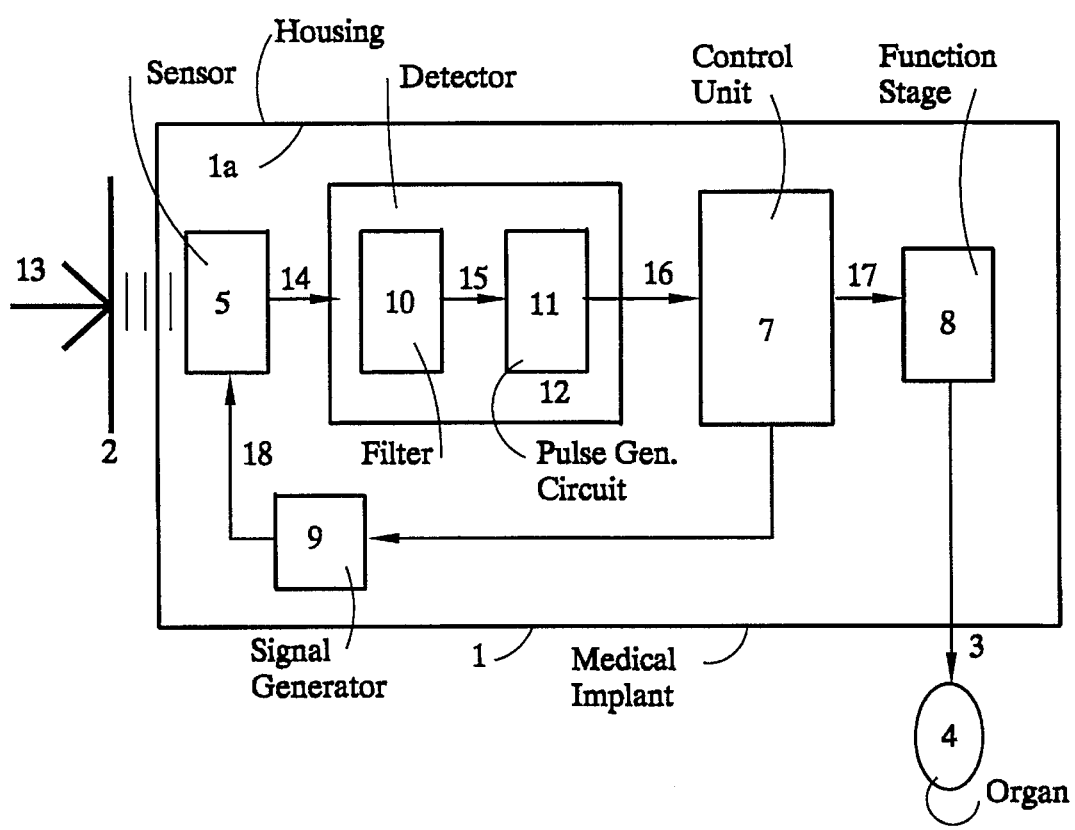

The drawing shows a medical implant 1 that is arranged under the skin 2 of a patient. The implant is connected for delivery of therapy to a human organ 4 via connector means 3. As already mentioned, the implant can be an insulin pump, whereby the connector means is a catheter that has been introduced into the abdominal cavity, or the implant can be a heart pacemaker or a defibrillator, whereby the connector 3 is an electrode lead that is conducted to the heart. The implant 1 has an implantable housing containing a sensor 5, a detector 6 that is coupled to the sensor 5, a control unit 7 that is connected to the detector 6, a function stage 8 connected to the control unit 7 to the human organ 4 via the connector 3, and a signal generator 9 connected to the control unit 7 and to the sensor 5. The detector 6 in turn includes a filter stage 10 and a pulse-generating circuit 11 having an adjustable threshold level 12. The function stage 8 effects or initiates a function of the implant, such as delivery of therapy, modification of a programmed therapeutic delivery schedule, etc. The function stage 8 can be responsible for only one function, in which case other function stages can be provided which are respectively responsible for other functions, or the function stage 8 can be responsible for a number of functions, dependent on the input signal supplied to the function stage 8.

Shockwaves 13 that are manually generated extracorporeally are sensed with the sensor 5, which generates corresponding electrical shockwave signals 14 that are supplied to the detector 14 wherein the electrical signals 14 are low-pass filtered in the filter stage 10. The filtered signals 15 are compared to the threshold level 12 in the pulse-generating circuit 11, whereby the circuit 11 emits pulses 16 to the control unit 7 if and when the filtered signals 15 exceed the threshold level 12.

In one embodiment, the duration between consecutive pulses 16 is measured in the control unit 7, and the measured time interval is compared to a predetermined, short, first time interval and to a predetermined, long, second time interval. Each duration is assigned to either the shorter or longer time interval, depending on which it more closely resembles. When all time intervals measured in a sequence can be assigned to the first or second time interval, (i.e., there are no "ambiguous" incoming intervals) this sequence of time intervals is compared to sequences of time intervals stored in the control unit 7 that respectively represent various functions of the medical implant 1. A sequence of measured time intervals is considered identified when it is found among the sequences stored in the control unit 7. When a sequence has been identified, the control unit 7 emits a function signal 17 to the function stage 8 for the implementation of the function of the implant 1 that corresponds to the sequence. The first and the second time intervals are individually set during the testing of the implant. These intervals cannot overlap and typical values can be 0.4 through 0.6 seconds for the first time interval and 0.8 through 1.5 seconds for the longer, second time interval or, for example, 0.5 through 1.5 seconds and 2.0 through 3.0 seconds, respectively.

The lower limit of the first interval must be significantly above the pulse length of the output pulse of the pulse-generating circuit, which typically has a pulse length of 100 ms.

According to an alternative embodiment, the time between consecutive pulses is measured in the control unit 7 and the measured time interval is compared to a predetermined time threshold. If and when all time intervals measured for a sequence of pulses fall below this threshold, the number of pulses belonging to the sequence is identified and this number is compared to numbers stored in the control unit 7 that respectively represent various functions of the medical implant 1. A sequence is considered identified when the number of pulses belonging to the sequence corresponds to one of the numbers stored in the control unit 7. When a sequence has been identified, the control unit 7 emits a function signal 17 to the function stage 8 for implementing the function of the implant 1 that corresponds to the sequence. The time threshold can be adapted at the request of the patient and can, for example, be 1.0 second.

In order to enhance the reliability when sensing the shockwave sequences and thus to avoid, for example, a pat on the back and other uncontrollable impacts to the body from being mistakenly interpreted by the implant 1 as a command, either of the above embodiments can be augmented with an acknowledgement procedure wherein the patient receives an acknowledgement or confirmation that the implant 1 has acquired the correct command. In this acknowledgement procedure a first sequence of shockwaves 13 must be generated for the implant 1 in order to enable the implant 1 to accept a second sequence of shockwaves 13 that corresponds to a function of the implant 1. After the generation of the first sequence, the second sequence of shockwaves 13 that defines a function of the implant is generated for the implant 1. The second sequence, in this procedure, causes the control unit 7 to instruct the signal generator 9 to emit a control signal 18, so that the sensor 5 is activated to send extracorporeally detectable signals corresponding to the second sequence as an acknowledgement that the generated second sequence corresponds to the intended sequence. The extracorporeally registrable signal can, for example, be an acoustic signal or signal sequence or a vibrational signal or signal sequence that can be understood by the patient. When the patient confirms, by means of this acknowledgement signal, that the sequence that has been sent by the sensor 5 corresponds to the intended sequence and when one still wishes to implement the function, then a third sequence of shockwaves is generated for the implant 1 as a command that the function corresponding to the second sequence should be implemented. This causes the control unit 7 to emit a function signal 17 for the implementation of the function corresponding to the second sequence to the function stage 8 when the control unit 7 identifies the received, third sequence as a command sequence.

A longest allowable time between the sequences can be specified in the acknowledgement procedure as set forth above. This time can be individually set and can, for example, be 10 seconds. This means that the acknowledge procedure is interrupted if a pause that exceeds 10 seconds between the shockwave sequences arises in an acknowledgement procedure.

The functions of the implant 1 that are suitable for being activated with the assistance of the method of the invention given an insulin pump can be included, for example, specifying the point in time for a mealtime dose, specifying the size of the dose and aborting a mealtime dose that had been begun.

The sensor 5 may be a piezoelectric crystal connected for receiving and emitting (transmitting) for sensing shockwaves as well as for generating extracorporeally detecting signals.

The pulse-generating circuit 11 in a preferred embodiment is a one-shot multivibrator, whereby the pulse 16 is a square-wave pulse. When trimming the circuitry, the threshold level 12 is set dependent on the patient's wishes. The threshold level 12 indicates the smallest amplitude that the filtered shockwave signal 15 can have in order to trigger the pulse-generating circuit 11 to emit a pulse. Accordingly, the threshold level 12 is set dependent on how "hard" an impact to the body one must produce in order for the impact to be registered as shockwaves 13. In an advantageous embodiment, the pulse generated by the circuit 11 has a specific length, for example 100 ms, independent of the shape of the filtered shockwave signal. A further possibility is instead to make the pulse length dependent on the length of a shockwave signal.

Most of the functions that the control device 7 implements ensue on the basis of software, for example the measuring of the time between consecutive pulses 16 that have been emitted by the detector 6, the interpretation of the received sequences, and the comparison of the received sequences to stored sequences.

A shockwave sequence can be composed, for example, of 2 through 10 shockwaves. It is possible to allow more shockwaves to belong to a sequence; however, it can then become difficult to memorize the sequence and to count correctly when generating the shockwaves. Which shockwave sequences respectively correspond to the functions of the implant is decided with input from the patient in conjunction with the programming of the control device 7.

The invention has been set forth herein in the context of an implantable insulin pump because such an application is easiest to understand. It is clear, however, that the invention is not limited to this application but, as set forth above, can be employed in conjunction with other implants, for example heart pacemakers or defibrillators.

Although modifications and changes may be suggested by those skilled in the art, it is the intention of the inventors to embody within the patent warranted hereon all changes and modifications as reasonably and properly come within the scope of their contribution to the art.

I claim as my invention:

1. A medical implant comprising:

an implantable housing;

function implementation means in said housing for implementing one of a plurality of functions relating to administration of therapy to a patient in whom said housing is implanted;

sensor means in said housing for sensing a series of extracorporeally generated shockwave pulses, said pulses having intervals therebetween, and for generating an electrical signal having a series of electrical pulses with respective intervals therebetween corresponding to the intervals between said shockwave pulses;

measuring means in said housing for measuring a duration of each interval in said electrical signal;

means in said housing for comparing the duration of each interval in said electrical signal, as measured by said measuring means, to each of a first predetermined time interval and a second predetermined time interval longer than said first predetermined interval, and for assigning each duration as being of said first predetermined time interval or of said second predetermined time interval and for producing an output interval sequence of first and second predetermined time intervals dependent on the comparison of the respective durations for all intervals in said electrical signal;

memory means in said housing for storing a plurality of interval sequences respectively corresponding to said plurality of functions;

means in said housing for comparing said output interval sequence to said interval sequences of said memory means for storing; and means in said housing for, if coincidence exists between said output interval sequence and one of said plurality of interval sequences, controlling said function implementation means to implement the function corresponding to said one of said plurality of interval sequences.

2. A medical implant as claimed in claim 1 further comprising:

means in said housing for comparing the respective durations of said intervals in said electrical signal to a predetermined threshold and, if all of said durations are below said predetermined time threshold, for determining a number of pulses in said electrical signal;

said memory means further comprising means for storing a plurality of numbers respectively corresponding to said functions; and means for comparing the number of pulses in said electrical signal to said numbers in said memory means and for accepting said electrical signal as valid if the number of pulses in said electrical signal coincides with one of said numbers in said memory means.

3. A medical implant as claimed in claim 1 further comprising:

filter means in said housing, supplied with said electrical signal, for filtering said electrical signal by comparing said electrical pulses in said electrical signal to an adjustable threshold level and for generating a filtered electrical signal containing only pulses which exceed said threshold level.

4. A medical implant as claimed in claim 3 further comprising:

signal generator means in said housing connected to said sensor means and to said means for controlling said function implementation means, for causing said sensor means to emit an extracorporeally detectable signal identifying the function implemented by said function implementation means.

5. A method for operating a medical implant implanted in a patient comprising the steps of:

extracorporeally generating a series of shockwave pulses in said patient, said pulses having intervals therebetween;

sensing said series of extracorporeally generated shockwave pulses in said medical implant generating an electrical signal having a series of electrical pulses with respective intervals therebetween corresponding to the intervals between said shockwave pulses;

measuring a duration in said medical implant of each interval in said electrical signal;

comparing, in said medical implant, the duration of each interval in said electrical signal to each of a first predetermined time interval and a second predetermined time interval longer than said first predetermined interval, and assigning each duration as being of said first predetermined time interval or of said second predetermined time interval and producing an output interval sequence of first and second predetermined time intervals dependent on the comparison of the respective durations for all intervals in said electrical signal;

storing a plurality of interval sequences in said medical implant respectively corresponding to a plurality of function relating to administration of therapy to said patient;

comparing, in said medical implant, said output interval sequence to said interval sequences stored in said medical implant; and if coincidence exists between said output interval sequence and one of said plurality of interval sequences, implementing the function corresponding to said one of said plurality of interval sequences.

6. A method as claimed in claim 5 comprising the further steps of:

comparing, in said medical implant, the respective durations of said intervals in said electrical signal to a predetermined threshold and, if all of said durations are below said predetermined time threshold, determining a number of pulses in said electrical signal;

storing a plurality of numbers in said medical implant respectively corresponding to said functions; and comparing, in said medical implant, the number of pulses in said electrical signal to said numbers in said memory means and accepting said electrical signal as valid if the number of pulses in said electrical signal coincides with one of said numbers in said memory means.

7. A method as claimed in claim 5 comprising the further steps of:

filtering said electrical signal in said medical implant by comparing said electrical pulses in said electrical signal to an adjustable threshold level and generating a filtered electrical signal containing only pulses which exceed said threshold level.

8. A method as claimed in claim 7 comprising the additional step of:

causing said sensor means to emit an extracorporeally detectable signal identifying the function implemented by said function implementation means.

* * * * *